United States Patent
Xie et al.

(10) Patent No.: US 6,692,126 B1
(45) Date of Patent: *Feb. 17, 2004

(54) METHOD AND APPARATUS FOR MEASURING A CORNEAL PROFILE OF AN EYE

(75) Inventors: Jing-Gang Xie, Pleasanton, CA (US); Ming Lai, Dublin, CA (US); Jay Wei, Fremont, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 85 days.

This patent is subject to a terminal disclaimer.

(21) Appl. No.: 10/051,192

(22) Filed: Jan. 17, 2002

Related U.S. Application Data

(63) Continuation-in-part of application No. 09/981,054, filed on Oct. 17, 2001, now Pat. No. 6,575,573.

(51) Int. Cl.[7] .................................................. A61B 3/10
(52) U.S. Cl. ........................................ 351/212; 351/214
(58) Field of Search ................................. 351/205, 206, 351/208, 211, 212, 214, 221, 246; 606/5

(56) References Cited

U.S. PATENT DOCUMENTS

| | | | |
|---|---|---|---|
| 2,174,308 A | 9/1939 | Hartinger | 88/20 |
| 3,248,162 A | 4/1966 | Knoll | 351/6 |
| 3,290,927 A | 12/1966 | Gambs | 73/80 |
| 3,486,812 A | 12/1969 | Volk | 351/6 |
| 3,536,384 A | 10/1970 | Cocks | 351/6 |
| 3,598,478 A | 8/1971 | Townsley | 351/6 |
| 3,609,017 A | 9/1971 | Nuchman | 351/13 |
| 3,634,003 A | 1/1972 | Guyton | 351/17 |
| RE27,475 E | 9/1972 | Volk | 351/39 |
| 3,797,921 A | 3/1974 | Kilmer et al. | 351/7 |
| 3,895,860 A | 7/1975 | Townsley | 351/39 |
| 3,932,030 A | 1/1976 | Hasegawa et al. | 351/6 |
| 4,019,813 A | 4/1977 | Cornsweet et al. | 351/14 |
| 4,157,859 A | 6/1979 | Terry | 350/35 |
| 4,159,867 A | 7/1979 | Achatz et al. | 351/6 |
| 4,172,639 A | 10/1979 | Lang et al. | 351/13 |
| 4,256,385 A | 3/1981 | Cohen et al. | 351/13 |
| 4,410,242 A | 10/1983 | Muller et al. | 351/211 |
| 4,420,228 A | 12/1983 | Humphrey | 351/212 |
| 4,426,141 A | 1/1984 | Holcomb | 351/212 |
| 4,456,348 A | 6/1984 | Schulz et al. | 351/212 |
| 4,490,022 A | 12/1984 | Reynolds | 351/212 |
| 4,491,398 A | 1/1985 | Karickhoff | 351/211 |
| 4,569,576 A | 2/1986 | Karpov et al. | 351/212 |
| 4,597,648 A | 7/1986 | Feldon et al. | 351/212 |
| 4,685,140 A | 8/1987 | Mount, II | 382/6 |
| 4,764,006 A | 8/1988 | Hamano et al. | 351/211 |
| 4,772,115 A | 9/1988 | Gersten et al. | 351/212 |
| 4,779,973 A | 10/1988 | Miller et al. | 351/212 |

(List continued on next page.)

*Primary Examiner*—George Manuel
(74) *Attorney, Agent, or Firm*—Michael B. Einschlag

(57) ABSTRACT

One or more embodiments of the present invention provide a method and apparatus to determine a corneal thickness profile of an eye. In particular, one embodiment of the present invention is a corneal diagnostic instrument including: (a) a Placido ring illuminator disposed to project a Placido ring image onto a cornea to generate a reflected Placido ring image; (b) multiple slit lamp projectors disposed to project slit light beams onto the cornea to generate slit light beam images; (c) a camera system optically disposed to detect the reflected Placido ring image and the slit light beam images; and (d) a controller, coupled to the slit lamp projectors, the Placido ring illuminator, and the camera system, to cause the slit light beam images and the reflected Placido ring image to be generated and detected in a predetermined sequence, wherein the controller is responsive to the detected reflected Placido ring image and the detected slit light beam images to determine a corneal thickness profile.

40 Claims, 6 Drawing Sheets

U.S. PATENT DOCUMENTS

| | | | |
|---|---|---|---|
| 4,799,784 A | 1/1989 | Safir | 351/212 |
| 4,834,529 A | 5/1989 | Barrett | 351/212 |
| 4,863,260 A | 9/1989 | Gersten et al. | 351/212 |
| 4,978,213 A | 12/1990 | El Hage | 351/212 |
| 4,995,716 A | 2/1991 | Warnicki et al. | 351/212 |
| 4,998,819 A | 3/1991 | Labinger et al. | 351/212 |
| 5,009,498 A | 4/1991 | Gersten et al. | 351/212 |
| 5,018,850 A | 5/1991 | Gersten et al. | 351/212 |
| 5,106,183 A | 4/1992 | Yoder, Jr. | 351/212 |
| 5,159,361 A | 10/1992 | Cambier et al. | 351/212 |
| 5,194,882 A | 3/1993 | Penney | 351/212 |
| 5,214,456 A | 5/1993 | Gersten | 351/212 |
| 5,227,818 A | 7/1993 | El Hage | 351/212 |
| 5,300,965 A | 4/1994 | Kitajima | 351/212 |
| 5,307,097 A | 4/1994 | Baker | 351/212 |
| 5,347,331 A | 9/1994 | Isogai et al. | 354/62 |
| 5,349,398 A | 9/1994 | Koester | 351/212 |
| 5,357,294 A | 10/1994 | Shimizu et al. | 351/212 |
| 5,384,608 A | 1/1995 | Gersten | 351/212 |
| 5,404,884 A | 4/1995 | Lempert | 128/665 |
| 5,406,342 A | 4/1995 | Jongsma | 351/212 |
| 5,412,441 A | 5/1995 | Tibbling et al. | 351/200 |
| 5,414,478 A | 5/1995 | van Gelderen | 351/212 |
| 5,416,539 A | 5/1995 | Gersten et al. | 351/212 |
| 5,418,582 A | 5/1995 | van Saarloos | 351/212 |
| 5,418,714 A | 5/1995 | Sarver | 364/413.13 |
| 5,475,452 A | 12/1995 | Kuhn et al. | 351/212 |
| 5,512,965 A | 4/1996 | Snook | 351/205 |
| 5,512,966 A | 4/1996 | Snook | 351/205 |
| 5,539,837 A | 7/1996 | Lindmark | 382/100 |
| 5,585,873 A | 12/1996 | Shalon et al. | 351/218 |
| 5,592,246 A | 1/1997 | Kuhn et al. | 351/212 |
| 5,663,781 A | 9/1997 | Wilms et al. | 351/206 |
| 5,838,811 A | 11/1998 | Lindmark | 382/100 |
| 5,847,804 A | 12/1998 | Sarver et al. | 351/206 |
| 5,861,955 A | 1/1999 | Gordon | 356/360 |
| 5,865,742 A | 2/1999 | Massie | 600/405 |
| 5,870,167 A | 2/1999 | Knopp et al. | 351/212 |
| 5,891,131 A | 4/1999 | Rajan et al. | 606/5 |
| 6,079,831 A | 6/2000 | Sarver et al. | 351/247 |
| 6,099,522 A | 8/2000 | Knopp et al. | 606/10 |
| 6,234,631 B1 | 5/2001 | Sarver et al. | 351/212 |
| 6,361,168 B1 * | 3/2002 | Fujieda | 351/208 |
| 6,585,723 B1 * | 7/2003 | Sumiya | 606/5 |
| 6,601,956 B1 * | 8/2003 | Jean et al. | 351/212 |

* cited by examiner 11
16  13

17

18

19

METHOD AND APPARATUS FOR MEASURING A CORNEAL PROFILE OF AN EYE

This is a continuation-in-part of a patent application entitled "Method and Apparatus for Measuring a Corneal Profile of an Eye" having Ser. No. 09/981,054 which was filed on Oct. 17, 2001 now U.S. Pat. No. 6,575,573.

TECHNICAL FIELD OF THE INVENTION

One or more embodiments of the present invention pertains to method and apparatus for measuring a corneal profile of an eye. In particular, one or more embodiments of the present invention relates to method and apparatus for measuring a corneal topography and a corneal thickness profile of an eye.

BACKGROUND OF THE INVENTION

Accurate measurement of a corneal topography and a corneal thickness profile is important for the safety and effectiveness of corneal refractive surgery. As is well known, the corneal topography (for example, curvature (slope) and elevation profiles) of an anterior surface of a cornea, can be provided by a corneal topographer. Further, it is also well known how to use ray-tracing algorithms to combine slit light beam images and the corneal topography to measure the corneal thickness profile.

For example, whenever a slit light beam is projected onto the cornea, and a cross section of the slit light beam on the cornea is viewed from an angle, the corneal thickness profile can be observed and analyzed. Further, if the projection angle and the viewing angle of the slit light beam are predetermined, and the corneal topography is measured, the corneal thickness profile of the cornea can be calculated from the measured width of the cross section of the intersection of the slit light beam on the cornea.

As disclosed in U.S. Pat. Nos. 5,512,965 and 5,512,966 (inventor Richard K. Snook, the "Snook" patents), slit light beam images are recorded by a video camera, and the recorded images are processed in a digital format to produce a corneal curvature profile and a corneal thickness profile. As disclosed, slit light beams are projected from two sides of an instrument axis, and slit light beam images are taken along the instrument axis. During the disclosed measurement procedure, the slit light beams are scanned across the cornea in a parallel direction, and a video image is taken at each step of the slit light beam scan positions. To obtain an accurate measurement of the corneal thickness profile, one needs an accurate measurement of the corneal topography with high spatial resolution. This, in turn, requires the corneal topography to be measured at a large number of points across the anterior surface of the cornea. Thus, as disclosed, a large number of slit light beam images are required to generate sufficient data to measure accurately the corneal topography and the corneal thickness profile. In practice, a commercial instrument based on the disclosed design principle takes some forty (40) images for each measurement, and as a result, the data acquisition process takes more than one second to complete.

In U.S. Pat. Nos. 6,079,831, 6,120,150, and 6,257,723 (inventors Edwin J. Sarver and Charles R. Broadus, the "Sarver et al." patents), device and method are disclosed for mapping a corneal topography of an eye using elevation measurements in combination with slope measurements. For example, in accordance with one method disclosed therein, elevation measurements of the eye are collected using a slit beam diffuse reflection system, such as an ORBSCAN™ device. An approximating b-spline surface is then fitted to the elevation measurements. Slope measurements of the eye are collected using a Placido-based reflective system, but the slope measurements are referenced to points on the b-spline surface. The elevation and slope measurements are then blended using weighted least squares fitting techniques. Finally, a new b-spline surface is fitted to the blended measurements. However, it would be desirable to improve on the accuracy of the corneal topography provided as taught in the Sarver et al. patents.

In light of the above, there is a need in the art for method and apparatus for measuring corneal profiles of an eye that can operate quickly with improved accuracy.

SUMMARY OF THE INVENTION

One or more embodiments of the present invention advantageously satisfy one or more of the above-identified needs in the art. Specifically, one embodiment of the present invention is a corneal diagnostic instrument that determines a corneal topography and a corneal thickness profile. In particular, one embodiment of the present invention comprises: (a) a Placido ring illuminator disposed to project a Placido ring image onto a cornea to generate a reflected Placido ring image; (b) multiple slit lamp projectors disposed to project slit light beams onto the cornea to generate slit light beam images; (c) a camera system optically disposed to detect the reflected Placido ring image and the slit light beam images; and (d) a controller, coupled to the slit lamp projectors, the Placido ring illuminator, and the camera system, to cause the slit light beam images and the reflected Placido ring image to be generated and detected in a predetermined sequence, wherein the controller is responsive to the detected reflected Placido ring image and the detected slit light beam images to determine a corneal thickness profile.

Another embodiment of the present invention is a corneal diagnostic instrument that comprises: (a) a corneal topographer that determines a corneal topography of an anterior surface of a cornea; (b) multiple slit lamp projectors disposed to project slit light beams onto the cornea to generate slit light beam images; (c) a camera system optically disposed to detect the slit light beam images; and (d) a controller, coupled to the slit lamp projectors, the corneal topographer, and the camera system, to cause, in a predetermined sequence, (i) the slit light beam images to be generated and detected, and (ii) the corneal topographer to obtain data used to determine the corneal topography, wherein the controller is responsive to the corneal topography and to the detected slit light beam images output from the camera to determine a corneal thickness profile.

DETAILED DESCRIPTION

Figure 1:
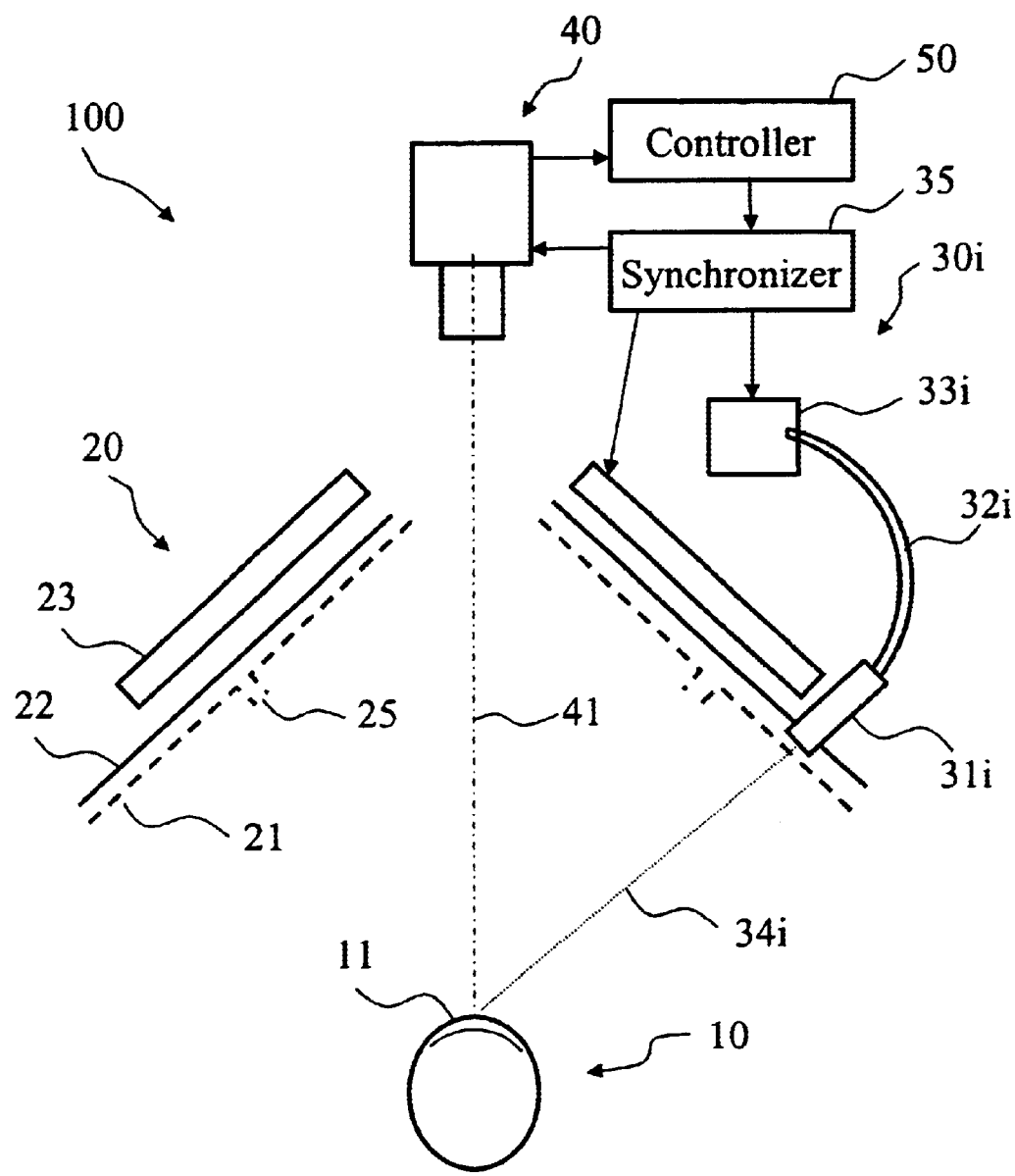
FIG. 1 is a schematic diagram of a corneal diagnostic instrument that is fabricated in accordance with one embodiment of the present invention.

FIG. 1 is a schematic diagram of corneal diagnostic instrument 100 that is fabricated in accordance with one embodiment of the present invention. As shown in FIG. 1, corneal diagnostic instrument 100 includes Placido ring illuminator 20, reference radiation source 25, camera system 40, a slit lamp projector assembly, synchronizer 35, and controller 50. In accordance with this embodiment of the present invention, the slit lamp projector assembly comprises a number of slit lamp projector sub-assemblies, but only slit lamp projector sub-assembly 30i is shown in FIG. 1 to make the embodiment more readily understandable, and not to obscure further details thereof.

In accordance with this embodiment of the present invention, a Placido ring image is formed by radiation output from Placido ring illuminator 20. The Placido ring image is reflected by cornea 11 of subject eye 10, and is detected by camera system 40. In one such embodiment shown in FIG. 1, Placido ring illuminator 20 comprises face plate 21 that is masked with Placido rings, diffuser plate 22, and illumination source 23. Face plate 21 determines the number and size of Placido rings in the Placido ring image, and diffuser plate 22 homogenizes radiation output from illumination source 23. Although face plate 21 shown in FIG. 1 is shown as a plane, embodiments of the present invention are not limited to the use a planar face plate. In fact further embodiments may be fabricated wherein face plate 21 has other shapes such as, for example, and without limitation, spherical or conical shapes. Illumination source 23 can be operated to output radiation, for example and without limitation, in the visible or in the near infrared spectrum. Although visible light is more commonly used, near infrared radiation may be useful since it is less noticeable to subject eye 10. Face plate 21, diffuser plate 22, and illumination source 23 may be fabricated in accordance with any one of a number of methods that are well known to those of ordinary skill in the art.

Reference radiation source 25 is disposed outside a Placido ring generation surface of Placido ring generator 20 (for example, for this embodiment, reference radiation source is disposed outside the surface of face plate 21 of Placido ring generator 20). Reference radiation source 25 may be a reference light point (for example, radiation is output from an end of an optical fiber) or it may be a reference ring of radiation. For an embodiment utilizing a reference light point, the reference light point is spaced from the faceplate relative to eye 10. For an embodiment utilizing a reference ring of radiation, the light emitting surface of the ring is not in the plane of the faceplate at any local tangent (for spherical and conical faceplates, "plane" means the local tangent plane adjacent to the reference light source along a line from cornea 11 to the reference light source). For example, if reference radiation source 25 is embodied as a reference ring of radiation, it may also be illuminated by illumination source 23. In any event, an image of reference radiation source 25 is reflected by cornea 11 of subject eye 10, and is detected by camera system 40. A relative apparent position of the image of reference radiation source 25 with respect to Placido rings in the Placido ring image provides a calibration reference (for example, a reference point or a reference ring, respectively) that varies with distance of cornea 11 from a reference point (for example, a center position of camera 40). In accordance with a technique disclosed in U.S. Pat. No. 5,418,582 (inventor Paul P. van Saarloos, the "Saarloos" patent), coordinates in space, and a tangent angle of a reflection point on the corneal anterior surface of an image of the reference radiation source are determined accurately. These coordinates and tangent angle are used to determine an actual distance from the reference point to an apex of the cornea. Advantageously, this enables the apparatus to achieve excellent accuracy in calculating the corneal topography of the corneal anterior surface (for example, curvature (slope) and elevation profiles).

The Placido ring image generated by Placido ring illuminator 20 is detected by camera system 40, and the Placido ring image output from camera system 40 is analyzed by controller 50 in accordance with any one of a number of methods that are well known to those of ordinary skill in the art to produce a corneal topography of an anterior surface (for example, curvature (slope) and elevation profiles) of cornea 11. In one embodiment, controller 50 is embodied as a computer, for example, a personal computer, and images output from camera system 40 are output to a frame grabber, and are accessible therefrom by the computer in accordance with any one of a number of methods that are well known to those of ordinary skill in the art. Lastly, as shown in FIG. 1, synchronizer 35 applies a signal to Placido ring illuminator 20, for example, to illumination source 23, to cause it to output radiation that generates the Placido ring image at a predetermined time. Synchronizer 35 may be fabricated in accordance with any one of a number of methods that are well known to those of ordinary skill in the art. In the embodiment shown in FIG. 1, synchronizer 35 receives a signal from controller 50 that causes synchronizer 35 to generate the appropriate signal it sends to illuminator 23 of Placido ring generator 20. Additionally, synchronizer 35 sends a signal to camera system 40 to cause it to operate so as to detect: (a) the Placido ring image generated by Placido ring illuminator 20 and reflected by cornea 11 and (b) the image generated by reference radiation source 25 and reflected by cornea 11. It should be understood that although synchronizer 35 is shown as being embodied separate from controller 50, further embodiments of the present invention exist wherein synchronizer 35 may form a portion of controller 50.

In accordance with one embodiment of the present invention, illumination source 23 is turned on to generate the Placido ring image and the image of reference radiation source 25, and it may be turned on for eye alignment. When it is turned on, Placido ring illuminator 20 and reference radiation source 25 illuminate eye 10. As a result, images of Placido rings and reference radiation source 25 are reflected by cornea 11, and are imaged on camera system 40. As shown in FIG. 1, camera system 40 is positioned to view cornea 11 along instrument axis 41. Instrument axis 41 is aligned with a visual axis of eye 10 in accordance with any one of a number of methods and mechanisms that are well known to those of ordinary skill in the art (such mechanisms are not shown for clarity and ease of understanding the principles of the present invention). Although camera system 40 is shown to be physically disposed along instrument axis 41, it should be appreciated that camera system 40 may be aligned at other positions. In that case, optical systems which are well known to those of ordinary skill in the art (for example and without limitation, beam splitting systems)

may be used to ensure that camera system 40 records images as if it were disposed as shown in FIG. 1, i.e., in such a case it may be said to be optically disposed along instrument axis 41.

Figure 2:
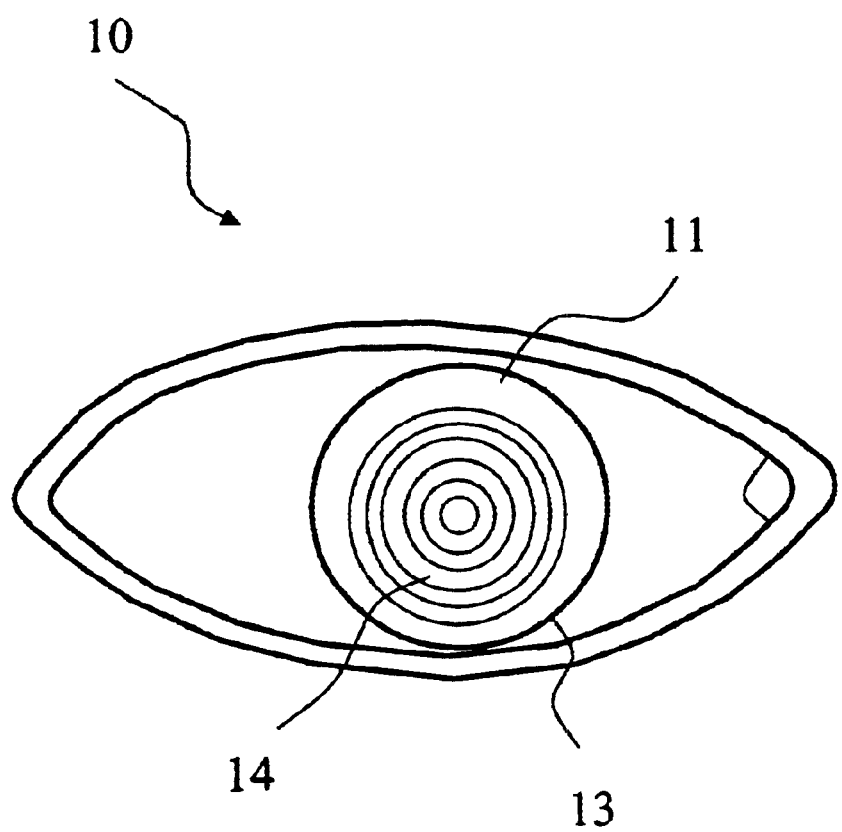
FIG. 2 is a pictorial representation of a Placido ring image obtained using the corneal diagnostic instrument shown in FIG. 1.

As is well known, the shape and size of each Placido ring carries position and curvature information of cornea 11 at the corresponding position. The Placido ring image produced by Placido ring illuminator 20 is detected by camera system 40, and is analyzed by controller 50 in accordance with any one of a number of methods that are well known to those of ordinary skill in the art to produce a corneal topography of an anterior surface of cornea 11. FIG. 2 is a pictorial representation of Placido ring image 14 obtained using corneal diagnostic instrument 100. In particular, FIG. 2 shows how Placido ring image 14 appears relative to other landmarks of eye 10. For example, the Placido rings are typically: (a) centered with a vertex of cornea 11; and (b) in alignment with, and located within, limbus 13 of eye 10. For a perfectly spherical corneal surface, all the Placido rings in Placido ring image 14 will be concentric circles. However, whenever cornea 11 deviates from a perfectly spherical surface, the Placido rings will bend and curve, depending on the local elevation and curvature (slope) of cornea 11.

As shown in FIG. 1, slit lamp projector sub-assembly 30$i$ comprises radiation source 33$i$, optical fiber 32$i$, and slit light projector 31$i$. Optical fiber 32$i$ delivers radiation output from radiation source 33$i$ to slit lamp projector 31$i$. Although slit light projector sub-assembly 30$i$ is shown to comprise optical fiber 32$i$, further embodiments of the present invention are not so configured, and can be fabricated without using an optical fiber to deliver radiation output from radiation source 33$i$ to slit light projector 31$i$.

In accordance with one embodiment of the present invention, each slit lamp projector 31$i$ includes a slit and imaging optics that images the slit onto cornea 11. Slit light beam 34$i$ output from slit light projector 31$i$ has a typical width of about 50 to about 100 microns on cornea 11, and a typical length of about 8 mm to about 10 mm on cornea 11. In one such embodiment, the slit width of slit lamp projector 31$i$ is about 10 microns, and its length is about 2 mm, and slit light beam 34$i$ output from slit light projector 31$i$ has a width of about 50 microns on cornea 11, and a length of about 10 mm on cornea 11. Further, the slit width of slit lamp projector 31$i$ may be about 10 microns to about 25 microns. Many methods are well known to those of ordinary skill in the art for fabricating the slit and the image optics of slit light projector sub-assemblies 30$i$.

Radiation source 33$i$ can comprise a flash lamp or a CW lamp or a light emitting diode ("LED"). In accordance with one embodiment of the present invention, each radiation source 33$i$ comprises a flash lamp that is synchronized with camera system 40 (in response to signals from synchronizer 35) for emission of radiation and for capture of images at predetermined times, respectively. In accordance with another embodiment of the present invention, radiation source 33$i$ comprises a CW lamp and an optical shutter (not shown). In such an embodiment, the optical shutter is synchronized with camera system 40 (in response to signals from synchronizer 35) for passing radiation at a predetermined time for a predetermined time period and for capture of images at predetermined times, respectively. In accordance with still another embodiment of the present invention, radiation source 33$i$ comprises an LED that is synchronized with camera system 40 (in response to signals from synchronizer 35) for emission of radiation and for capture of images at predetermined times, respectively. In the embodiment shown in FIG. 1, synchronizer 35 receives a signal from controller 50 that causes synchronizer 35 to generate the appropriate signal it sends to each radiation source 33$i$ and camera system 40. It should be understood that although synchronizer 35 is shown as being embodied separate from controller 50, further embodiments of the present invention exist wherein synchronizer 35 may form a portion of controller 50. In various embodiments, radiation source 331 may be a CW arc lamp, a CW halogen lamp, or a xenon flash lamp.

Figure 4:
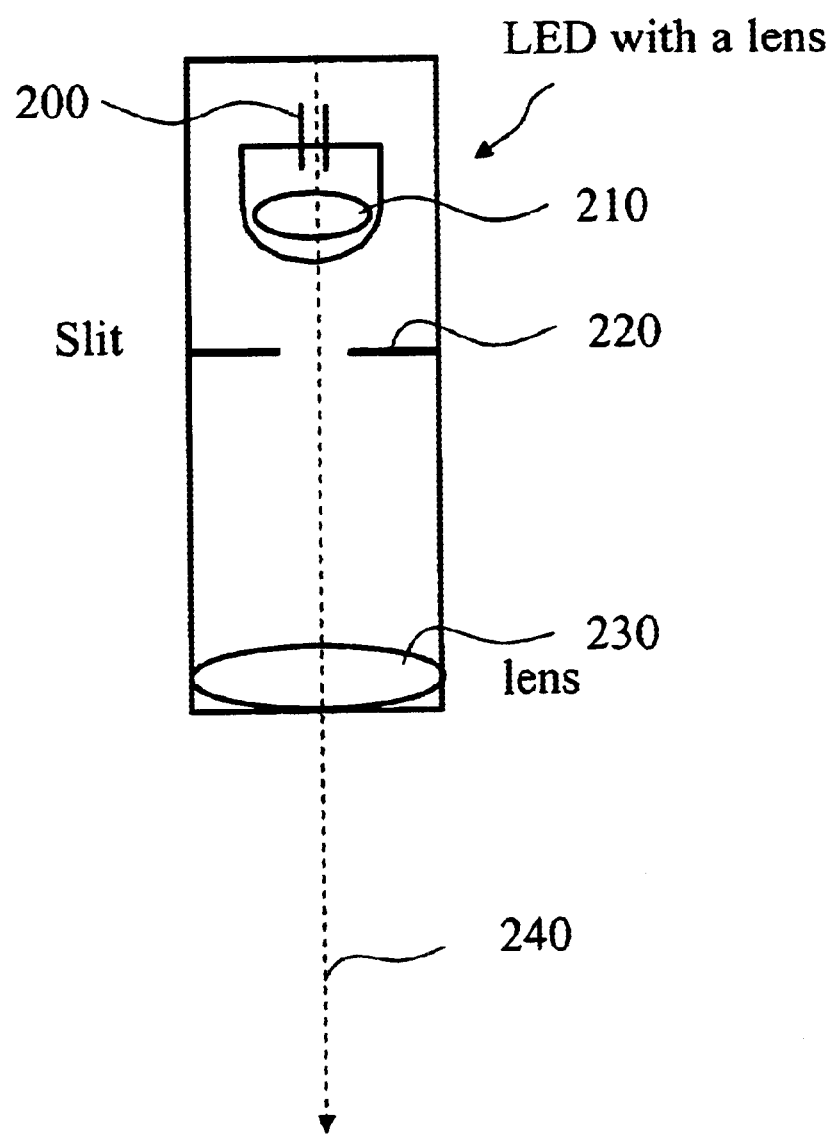
FIG. 4 is a pictorial representation of a slit light projector that is illuminated by a light emitting diode in accordance with one embodiment of the present invention.

For the embodiment shown in FIG. 1, optical fiber 32$i$ can be a large core, plastic fiber. In one such embodiment, the core size of optical fiber 32$i$ may be about 2 mm. In accordance with the embodiment of the present invention shown in FIG. 1, use of optical fiber 32$i$ enables slit light projector 31$i$ to be separated from radiation source 33$i$. This may be advantageous because it is easy to install and align slit light projector 31$i$, and to replace a lamp included in radiation source 33$i$. On the other hand, a flash lamp or an LED can be used to illuminate the slit light projector directly (i.e., without using an optical fiber. In this case, the slit light projectors may be more compact. FIG. 4 shows a pictorial representation of slit light projector illuminated by an LED in accordance with one embodiment of the present invention. As shown in FIG. 4, radiation output from LED 200 is collimated by lens 210 in accordance with any one of a number of methods that are well known to those of ordinary skill in the art. The collimated radiation passes through slit 220, is focused by lens 230 in accordance with any one or a number of methods that are well known to those of ordinary skill in the art to provide slit beam 240.

In accordance with one embodiment of the present invention, slit light projectors 31$i$ are installed around a circle in a plane that intersects face plate 21 and that is substantially perpendicular to instrument axis 41. However, the present invention is not thusly limited, and includes embodiments wherein the slit light projectors are not all in a plane or in a circle in a plane. In accordance with one such embodiment, slit light projectors 31$i$ are installed such that each slit-light beam 34$i$ has substantially the same projection angle on cornea 11, i.e., the same intersection angle with respect to instrument axis 41 shown in FIG. 1. In one such embodiment, each slit light beam 34$i$ is aligned such that it intersects instrument axis 41 at approximately 45 degrees, and such that it intersects cornea 11 substantially at its center. However, the present invention is not thusly limited, and includes embodiments wherein the projection angles of at some or all of the slight light beams are different.

In one embodiment of the present invention, the number of slit light beams 34$i$ is 4 to 8, which number of slit light beams 34$i$ can produce sufficient data and spatial resolution to produce an accurate corneal thickness profile. In such an embodiment, an angular spacing between slit light beams 34$i$ is uniform on a corneal plane, for example, a 45 degree angular spacing for an embodiment having 4 slit light beams 34$i$ and a 22.5 degree angular spacing for an embodiment having 8 slit light beams, the angular spacing being referred to as clocking angles. This is understood as follows. Each slit light beam intersects the cornea and appears as an image across the cornea. Therefore, four (4) slit light beams divide the cornea into 8 sections, and each section occupies a clocking angle of 45 degrees.

The radiation spectrum of slit light beams 34$i$ can include almost any radiation wavelength, but is preferably in the visible or near infrared. White light is commonly used in slit lamp examinations, and provides an acceptable choice for use in fabricating embodiments of the present invention.

However, blue light can also be an acceptable choice since scattering from corneal tissue is stronger for shorter wavelengths. Ultraviolet light may be used but may be less favorable due to its potential for causing damage to the eye. Near infrared radiation also provides an acceptable choice, and it is less noticeable to subject eye 10 than white or blue light.

In accordance with one embodiment of the present invention, camera system 40 is a CCD camera, and in another embodiment, camera system 40 is a video camera. In practice, the Placido ring image produced by Placido ring illuminator 20 and the slit light beam images produced by the slit lamp projector assembly are located on slightly different planes. To obtain the best quality images, one may use a camera system that comprises one camera to record the Placido ring image, and another camera to record the slit light beam images. For example, to do this, camera system 40 may further comprise a beam splitter (it can be installed in front of camera system 40 as shown in FIG. 1) to introduce a beam path for a second camera. Alternatively, one can adjust the focal plane of camera system 40 between times of obtaining the Placido ring image and the slit light beam images. To do this, camera system 40 may include a movable lens (it can be installed in front of camera system 40, i.e., between eye 10 and camera 40 as shown in FIG. 1) to adjust the image plane in a predetermined manner. Many methods are well known to those of ordinary skill in the art for fabricating a moving a lens. For example, in some such embodiment, the lens may be moved by a linear motor in response to signals from controller 50.

When a camera system comprised of two cameras is used, the spectrum of the illumination beam used to generate the Placido ring image can be chosen to be different from the spectrum of the illumination beams used to generate the slit light beam images. Thus, the image beam path for the first camera can be separated from that for the second camera by a dichromatic beam splitter. In this way, the Placido ring image can be captured at substantially the same time as any one of the slit light beam images is captured. In addition, in a further embodiment, the spectra of the illumination beams used to generate the slit images can be chosen so that the spectra are different from one another, or the spectra of predetermined ones are different from other predetermined ones. Then, images having different spectra can be captured in different cameras of a camera system wherein the image beam paths for the different cameras are separated using beam splitters and filters in accordance with any one of a number of methods that are well known to those of ordinary skill in the art. Lastly, the image beams having different spectra can be detected at the same time.

Figure 3A:
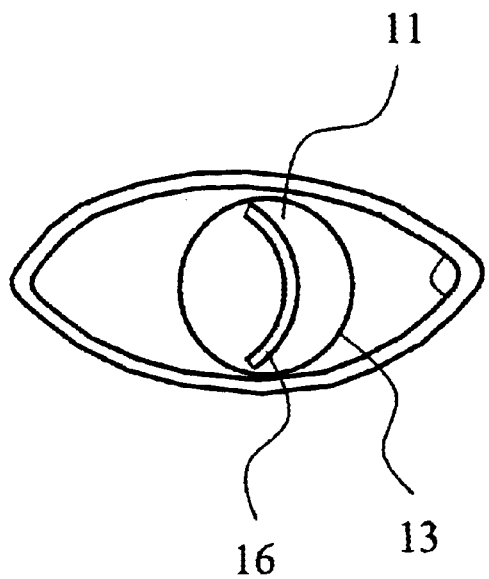
FIGS. 3a–3d are pictorial representations of four (4) slit light beam images obtained utilizing slit light beams projected from different clocking angles onto a cornea of an eye in accordance with one embodiment of the present invention.
Figure 3B:
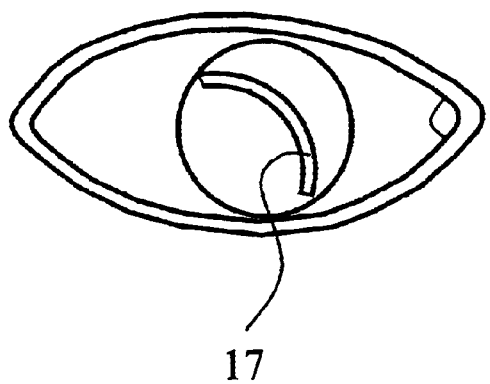
Figure 3C:
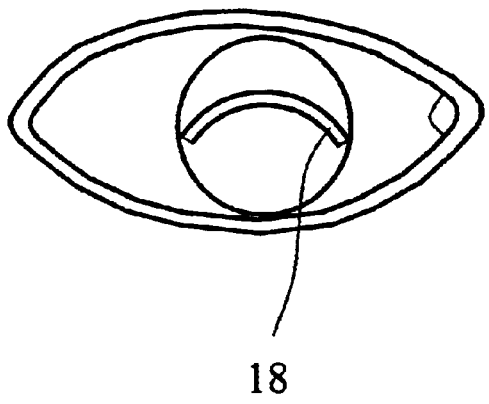
Figure 3D:
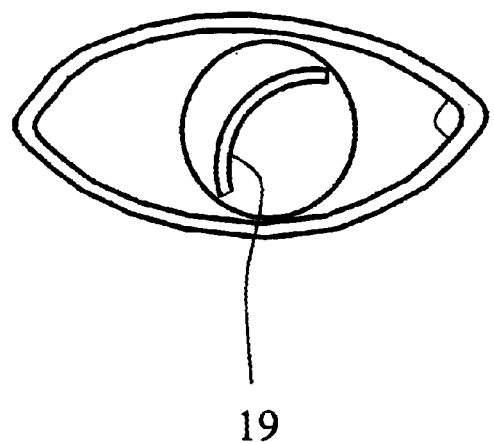

FIGS. 3a–3d are pictorial representations of four (4) slit light beam images obtained utilizing slit light beams projected from different clocking angles onto cornea 11. FIG. 3a shows slit light beam image 16 (at a viewing angle approximately along an axis of eye 10) that is formed when a slit light beam intersects eye 10 approximately at a center of cornea 11. To form slit light beam image 16 of FIG. 3a, the slit light beam is projected: (a) from a position to the right of eye 10; and (b) towards eye 10 at a predetermined angle (for example, an angle of approximately 45 degrees) with respect to the visual axis of eye 10. As is well known, the width of slit light beam image 16 is proportional to the corneal thickness, provided the width of the slit light beam is known, and provided that the width is much thinner than the corneal thickness. To calculate the corneal thickness from slit light beam image 16, the viewing angle at which the image was taken, and the projection angle of the slit light beam are predetermined. Also a local curvature (slope) and elevation of cornea 11 at every image point along slit light image 16 must be determined to enable ray tracing, through refraction, on an anterior surface of cornea 11. The principles involved in, and algorithms for using, ray tracing to determine corneal thickness are well known to those of ordinary skill in the art. For example, one can refer to U.S. Pat. Nos. 5,512,965 and 5,512,966. Similarly, FIGS. 3b–3d show slit light beam images 17–19, respectively, (at a viewing angle approximately along an axis of eye 10) that are formed when slit light beams intersect eye 10 approximately at the center of cornea 11. To form slit light beam image 17 of FIG. 3b, the slit light beam is projected: (a) from a position to the right and above eye 10; and (b) towards eye 10 at a predetermined angle (for example, an angle of approximately 45 degrees) with respect to the axis of eye 10. To form slit light beam image 18 of FIG. 3c, the slit light beam is projected: (a) from a position above eye 10; and (b) towards eye 10 at an angle of approximately 45 degrees with respect to the axis of eye 10. To form slit light beam image 19 of FIG. 3d, the slit light beam is projected: (a) from a position to the left and above eye 10; and (b) towards eye 10 at a predetermined angle (for example, an angle of approximately 45 degrees) with respect to the axis of eye 10.

In operation, in accordance with one embodiment of the present invention, Placido ring illuminator 20 and each slit lamp projector sub-assembly 30$i$, for example, slit light projectors 31$i$ thereof, are turned on, for example, one at a time, in a predetermined sequence, which predetermined sequence is synchronized with camera system 40, to generate a Placido ring image and a plurality of slit light beam images. These slit light beam images can then be used by controller 50, in combination with the corneal topography (for example, curvature (slope) and elevation profiles) of the anterior surface of cornea 11 generated by analyzing the Placido ring image, to generate a corneal thickness profile. An algorithm for use in generating the corneal thickness profile may be based on triangular ray tracing, and a number of such algorithms are well known to those of ordinary skill in the art.

The following describes an algorithm used to provide a corneal thickness profile in accordance with one embodiment of the present invention. Pre-calibrated system parameters include principal planes of camera system 40, a position of the apex of cornea 11 relative to a reference point (for example, a position of a center of camera system 40), azimuthal and polar incident angles of the slit beams, the refractive indices for air and 10 cornea 11 (for example, in one embodiment $n_{air}=1$, and $n_{cornea}=1.376$, respectively).

Step 1: Obtain a corneal topography of the corneal anterior surface (for example, curvature (slope) and elevation profiles) in accordance with the description set forth above.

Figure 7:
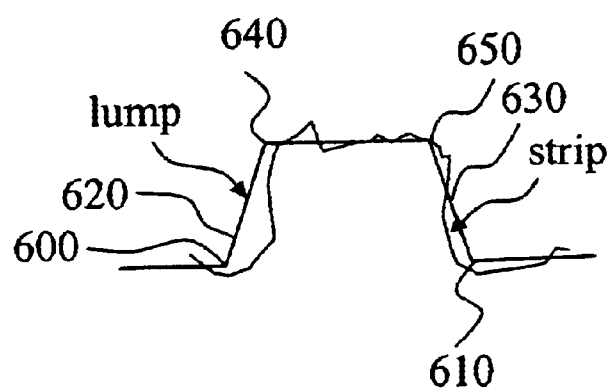
FIG. 7 illustrates a strip-lump-fit algorithm used in accordance with one embodiment of the present invention.

Step 2: Determine edges of a slit beam image detected by camera system 40 (a first edge represents an interface of the anterior surface of cornea 11 with a slit beam, and a second edge represents an interface of the posterior surface of cornea 11 with the slit beam) in accordance with any one of a number of methods that are well known to those of ordinary skill in the art. For example, intensity adjustment, gamma correction, filtering, dilation and erosion are common techniques used for detecting the image edges. For slit beam images with poor image quality, for example, images having non-uniform intensity distributions, the edges may be hard to define. In such a case, a strip-lump-fit algorithm may be used to help detect interface edges of the anterior surface and the posterior surface of cornea 11 with the slit beam. In accordance with this strip-lump-fit algorithm, sections of a slit beam image are taken (each section being referred to herein as a "strip"), and, for example, a trapezoidal shape (referred to herein as a "lump") is used as an approximation of the intensity distribution of each strip. In accordance with this algorithm, the shape of a lump is optimized by searching for: (a) starting and ending points of the trapezoid (points 600 and 610 in FIG. 7), (b) the slopes of the rising and falling edges of the trapezoid (edges 620 and 630 in FIG. 7), and (c) a plateau height of the trapezoid (defined by points 640 and 650 in FIG. 7) that minimize a difference in area between the lump and the strip.

Step 3: Fit each edge to a polynomial in accordance with any one of a number of methods that are well known to those of ordinary skill in the art.

Figure 5:
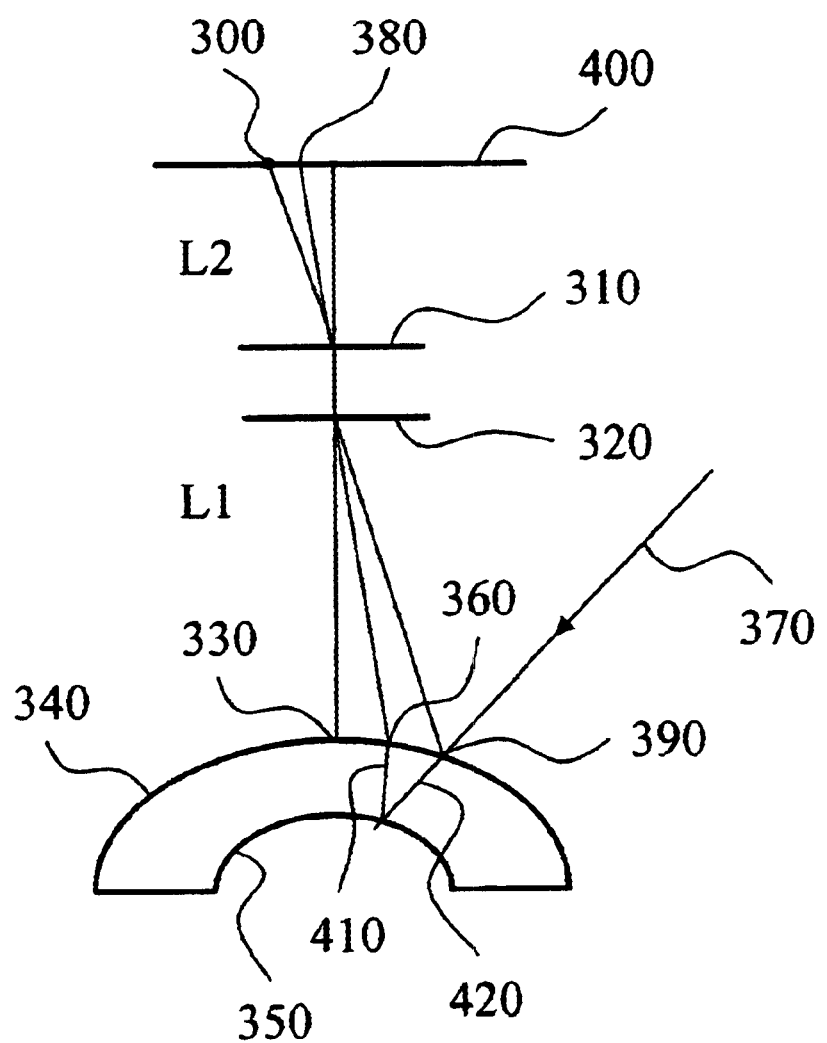
FIG. 5 illustrates ray tracing in accordance with one embodiment of the present invention.

Step 4: Select a point on the first polynomial curve (corresponding to the interface of the slit beam with the anterior surface). Referring to FIG. 5, construct a chief ray from the selected point (point 300 disposed on CCD sensor surface 400) through camera system 40, which chief ray is a reflection of the slit beam at the anterior surface using ray tracing in accordance with methods that are well known to those of ordinary skill in the art. A lens of camera system 40 is represented by principal planes 310 and 320, where principal plane 310 is located at a distance L2 from surface 400 (L2 is a predetermined distance) and where principal plane 320 is located at a distance L1 from apex 330 of corneal anterior surface 340 (L1 is determined using reference light source 25 in accordance with the above-described method). Point of intersection 390 of the chief ray with anterior surface 340 is calculated using the anterior surface elevation profile. Then, slit beam 370 is refracted into cornea 11 using Snell's law, the incident angle of slit beam 370 (known from pre-calibration, see above), and the local anterior surface curvature at intersection point 390 (known from the corneal topography).

Step 5: Select a point on the second polynomial curve (point 380 disposed on CCD sensor surface 400 corresponds to the interface of slit beam 370 with posterior surface 350). Apply similar ray tracing through camera system 40 to intersection point 360 with anterior surface 340 (point of intersection 360 of the chief ray with anterior surface 340 is calculated using the anterior surface elevation profile). Then, the chief ray is refracted into cornea 11 using Snell's law, the incident angle of the chief ray, and the local anterior surface curvature at intersection point 360 (known from the corneal topography).

Step 6: Determine whether the two rays intersect within cornea 11. To do this, calculate a minimum distance between the two refracted rays (rays 410 and 420). If the minimum distance is equal to, or close to (within a predetermined amount that is determined by the measurement uncertainties of the apparatus), zero within cornea 11, points 300 and 380 are correlated with each other in that their intersection defines a point on the corneal posterior surface. In other words, whenever slit beam 370 is projected at anterior surface 340, intersection point 390 of slit beam 370 with anterior surface 340 is recorded by camera system 40 at a point on the first polynomial curve. Incident slit beam 370 is refracted into cornea 11, and an intersection point of the refracted ray with posterior surface 350 is recorded by camera system 40 at a point on the second polynomial curve. Thus, the two points are correlated with each other.

Figure 6:
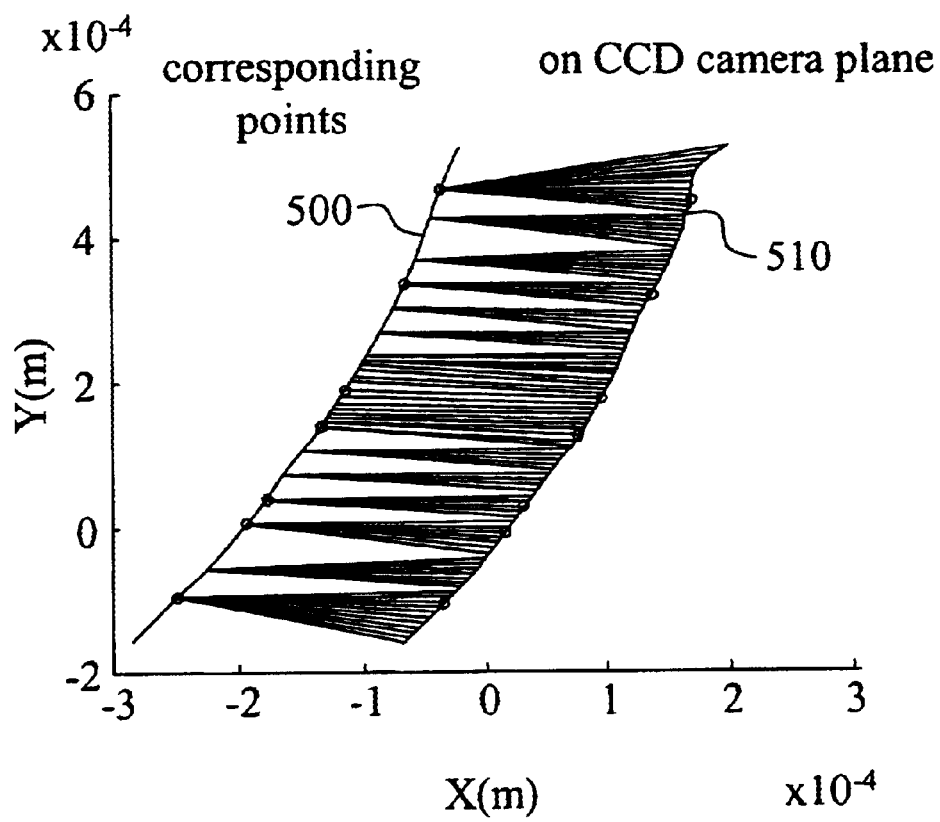
FIG. 6 illustrates a process of searching for correlated points in accordance with one embodiment of the present invention.

Step 7: If the minimum distance between refracted rays 410 and 420 is greater than the predetermined amount, the two selected points (from the first polynomial curve and the second polynomial curve, respectively) are not correlated. Then another point from the second polynomial curve is selected, and the intersection searching procedure is repeated. FIG. 6 illustrates the process of searching for correlated points where curve 500 represents the first polynomial curve, and curve 510 represents the second polynomial curve.

Step 8: Move to other points on the first polynomial curve, and repeat the above-described steps.

Step 9: Process all of the slit beam images in accordance with the above-described steps to define many points on the posterior surface. Then, determine a complete map of the posterior surface by, for example, bilinear interpolation of these points. Many other methods for developing the complete map of the posterior surface may also be used by those of ordinary skill in the art.

Step 10: The corneal thickness is defined as a distance from the corneal anterior surface along a normal to the corneal posterior surface. Since maps for the corneal anterior surface and the corneal posterior surface have been determined, a thickness profile of the cornea can be calculated therefrom in accordance with any one of a number of methods that are well known to those of ordinary skill in the art.

Advantageously, in accordance with one or more embodiments of the present invention, when corneal diagnostic instrument 100 comprises Placido ring illuminator 20 (as shown in FIG. 1), this can significantly reduce the data acquisition time when compared with the data acquisition time for designs disclosed in U.S. Pat. Nos. 5,512,965 and 5,512,966. This is because, for example, use of Placido ring illuminator 20 can generate a great deal of data points at high spatial resolution in a single image. This is advantageous for the additional reason that, since all the data points for measuring the corneal topography are recorded in a single image, eye movement plays no effect on the precision of the measurement.

Further, in practice, the required number of data points and the required spatial resolution of the corneal topography (for example, curvature (slope) and elevation profiles) of the corneal anterior surface are much greater than that required to measure a corneal thickness profile. Thus, once a precise corneal topography is obtained, an accurate, measurement of the corneal thickness profile (along one cross section) can be obtained regardless of the number of slit light beam images used.

Although FIG. 1 shows an embodiment wherein the Placido ring image and the slit light beam images are obtained using the same camera and are analyzed in the same controller, further embodiments of the present invention exist wherein the Placido ring image and the slit light beam images are captured in separate (even multiple separate) cameras, and are analyzed in the same or separate controllers.

In another embodiment of the present invention, the corneal diagnostic instrument would comprise a corneal topographer that generates a corneal topography of an anterior surface of a cornea (for example, curvature (slope) and elevation profiles), a camera system (for example, a camera system like that shown in FIG. 1, and/or described above), a slit lamp projector assembly (for example, a slit lamp projector assembly like that shown in FIG. 1, and/or described above), a synchronizer (for example, a synchronizer like that shown in FIG. 1, and/or described above), and a controller (for example, a controller like that shown in FIG. 1, and/or described above). In operation, in accordance with one such embodiment of the present invention, the corneal topographer and each slit lamp projector subassembly of the slit lamp projector assembly are turned on, for example, one at a time, in a predetermined sequence, which predetermined sequence is synchronized with camera system 40, to generate information used to provide a corneal topography and a plurality of slit light beam images. Then, the slit light beam images can be used by the controller, in combination with the corneal topography, to generate a corneal thickness profile, for example, in accordance with the methods described above.

Those skilled in the art will recognize that the foregoing description has been presented for the sake of illustration and description only. As such, it is not intended to be exhaustive or to limit the invention to the precise form disclosed. For example, in some embodiments described above, the term predetermined sequence may include generating and detecting a Placido ring image before generating and detecting slit light beam images, or vice versa, or some other sequence. Note that the term sequence is not restricted to a meaning of one thing after another, but is used in a more general sense. That is, the term sequence can include events where things happen at the same time, or where some things happen at the same time and others things happen one after another.

What is claimed is:

1. A corneal diagnostic instrument that comprises:
    a Placido ring illuminator disposed to project a Placido ring image onto a cornea to generate a reflected Placido ring image;
    multiple slit lamp projectors disposed to project slit light beams onto the cornea to generate slit light beam images;
    a camera system optically disposed to detect the reflected Placido ring image and the slit light beam images; and
    a controller, coupled to the slit lamp projectors, the Placido ring illuminator, and the camera system, to cause the slit light beam images and the reflected Placido ring image to be generated and detected in a predetermined sequence, wherein the controller is responsive to the detected reflected Placido ring image and the detected slit light beam images to determine the corneal thickness profile.

2. The corneal diagnostic instrument of claim 1 wherein at least one of the multiple slit lamp projectors comprises a flash lamp.

3. The corneal diagnostic instrument of claim 1 wherein at least one of the multiple slit lamp projectors comprises an optical fiber.

4. The corneal diagnostic instrument of claim 3 wherein the optical fiber has a large core.

5. The corneal diagnostic instrument of claim 4 wherein the core is about 2 mm.

6. The corneal diagnostic instrument of claim 1 wherein at least one of the multiple slit lamp projectors comprises a CW light source.

7. The corneal diagnostic instrument of claim 1 wherein at least one of the multiple slit lamp projectors comprises a light emitting diode.

8. The corneal diagnostic instrument of claim 1 wherein each of the multiple slit lamp projectors project a slit light beam at a substantially predetermined constant angle with respect to a predetermined axis.

9. The corneal diagnostic instrument of claim 1 wherein each of the multiple slit lamp projectors projects a slit light beam with a uniform clocking angle separation from each other.

10. The corneal diagnostic instrument of claim 1 wherein at least one of the multiple slit lamp projectors projects a slit light beam having a white light spectrum.

11. The corneal diagnostic instrument of claim 1 wherein at least one of the multiple slit lamp projectors projects a slit light beam having a blue light spectrum.

12. The corneal diagnostic instrument of claim 1 wherein at least one of the multiple slit lamp projectors projects a slit light beam having an infrared spectrum.

13. The corneal diagnostic instrument of claim 1 wherein the multiple slit lamp projectors comprises 4 to 8 projectors.

14. The corneal diagnostic instrument of claim 1 wherein the controller comprises a synchronizer that causes the slit light beam images and the reflected Placido ring image to be generated and detected in a predetermined sequence.

15. The corneal diagnostic instrument of claim 1 wherein the predetermined sequence causes the reflected Placido ring image to be generated and detected before the slit light beam images are generated and detected.

16. The corneal diagnostic instrument of claim 1 wherein the predetermined sequence causes the reflected Placido ring image to be generated and detected after the slit light beam images are generated and detected.

17. The corneal diagnostic instrument of claim 1 wherein:
    the Placido ring illuminator projects radiation comprising first wavelengths and the slit light beams comprise radiation having second wavelengths, wherein the first and second wavelengths are different; and
    the camera system comprises a first camera that detects radiation having the first wavelengths and a second camera that detects radiation having the second wavelengths.

18. The corneal diagnostic instrument of claim 17 wherein:
    the controller provides the predetermined sequence wherein the reflected Placido ring image is generated and detected in the first camera during at least a portion of time that the slit light beam images are generated and detected in the second camera.

19. The corneal diagnostic instrument of claim 1 wherein the camera system comprises a movable lens.

20. The corneal diagnostic instrument of claim 1 which further comprises a reference radiation source disposed outside a local tangent plane of the Placido ring illuminator so that the camera system detects an image of a reflection of the reference radiation from the cornea; and the controller is responsive to the detected reflected reference image, the detected reflected Placido ring image, and the detected slit light beam images to determine the corneal thickness profile.

21. The corneal diagnostic instrument of claim 1 which further comprises a reference radiation source that is displaced outside a Placido ring generation surface of the Placido ring illuminator.

22. The corneal diagnostic instrument of claim 21 wherein the reference radiation source comprises a reference light point.

23. The corneal diagnostic instrument of claim 21 wherein the reference radiation source comprises a reference ring of radiation wherein the light emitting surface of the ring is not in the plane of faceplate of the Placido ring illuminator at any local tangent.

24. The corneal diagnostic instrument of claim 23 wherein the faceplate is spherical or conical and the plane is the local tangent plane adjacent to the reference radiation source along a line from the cornea to the reference radiation source.

25. A corneal diagnostic instrument that comprises:
a corneal topographer that determines a corneal topography of an anterior surface of a cornea;
multiple slit lamp projectors disposed to project slit light beams onto the cornea to generate slit light beam images;
a camera system optically disposed to detect the slit light beam images; and
a controller, coupled to the slit lamp projectors, the corneal topographer, and the camera system, to cause, in a predetermined sequence, (a) the slit light beam images to be generated and detected, and (b) the corneal topographer to obtain data used to determine the corneal topography, wherein the controller is responsive to the detected slit light beam images and the corneal topography to determine a corneal thickness profile.

26. The corneal diagnostic instrument of claim 25 wherein the corneal topographer generates a Placido ring image.

27. A method for corneal diagnosis that comprises steps of:
in a predetermined sequence, projecting a Placido ring image from a Placido ring illuminator and multiple slit light beams onto a cornea to generate a reflected Placido ring image and slit light beam images, and detecting the reflected Placido ring image and the slit light beam images; and
analyzing the detected reflected Placido ring image and the detected slit light beam images to determine a corneal thickness profile.

28. The method of claim 27 wherein the step of projecting multiple slit light beams includes generating the slit light beams utilizing at least one flash lamp.

29. The method of claim 27 wherein the step of projecting multiple slit light beams includes generating the slit light beams utilizing at least one optical fiber.

30. The method of claim 27 wherein the step of projecting multiple slit light beans includes generating the slit light beams utilizing at least one CW light source.

31. The method of claim 27 wherein the step of projecting multiple slit light beams includes generating the slit light beams utilizing at least one light emitting diode.

32. The method of claim 27 wherein the step of projecting multiple slit light beams includes projecting the slit light beams at a substantially predetermined constant angle with respect to a predetermined axis.

33. The method of claim 27 wherein the step of projecting multiple slit light beams includes projecting the slit light beams with a uniform clocking angle separation one another.

34. The method of claim 27 wherein the step of projecting multiple slit light beams includes projecting at least one slit light beam having a white light spectrum.

35. The method of claim 27 wherein the step of projecting multiple slit light beams includes projecting at least one slit light beam having a blue light spectrum.

36. The method of claim 27 wherein the step of projecting multiple slit light beams includes projecting at least one slit light beam having an infrared light spectrum.

37. The method of claim 27 wherein the step of projecting multiple slit light beams includes projecting 4 to 8 slit light beams.

38. The method of claim 27 which further includes a step of projecting radiation from a reference radiation source disposed outside a local tangent plane of the Placido ring illuminator onto the cornea to generate a reflected reference image, and detecting the reflected reference image; and analyzing the detected reflected reference image, the detected reflected Placido ring image, and the detected slit light beam images to determine the corneal thickness profile.

39. A method for corneal diagnosis comprise steps of:
utilizing a corneal topographer to obtain a corneal topography of an anterior surface of a cornea;
in a predetermined sequence, projecting multiple slit light beams onto the cornea to generate slit light beam images, and detecting the reflected slit light beam images; and
analyzing the corneal topography and the slit light beam images to determine a corneal thickness profile.

40. The method of claim 39 wherein the step of analyzing comprises steps of:
for each slit light beam image:
a. fitting a first edge of the slit light beam image to a first polynomial curve and a second edge of the slit light beam image to a second polynomial curve;
b. selecting a point on the first polynomial curve, and constructing a chief ray into the cornea from the selected point through a camera system that detects the reflected slit light beams;
c. selecting a point on the second polynomial curve, and constructing a chief ray into the cornea from the selected point through the camera system;
d. determining whether the two chief rays intersect within the cornea to determine whether the two points are correlated to each other; if they are not correlated, steps c and d are repeated; and
e. moving to other points on the first polynomial curve, and repeating steps c and d;
processing all the slit light beams to define a predetermined number of points on a posterior surface of the cornea;
determining a map of the posterior surface of the cornea using the predetermined points;
determining a corneal thickness as a distance from the corneal anterior surface along a normal to the corneal posterior surface; and
determining a thickness profile from a predetermined number of corneal thicknesses.

* * * * *